US006300125B1

(12) United States Patent
Saint-Ramon et al.

(10) Patent No.: US 6,300,125 B1
(45) Date of Patent: Oct. 9, 2001

(54) STRAW WITH ADAPTER INSERT

(75) Inventors: Jean-Gérard Saint-Ramon, L'Aigle; Christian Beau, Voisins-le-Bretonneux; Alain Ehrsam, Lyons, all of (FR)

(73) Assignee: IMV Technologies, L'Aigle (FR)

( * ) Notice: Subject to any disclaimer, the term of this patent is extended or adjusted under 35 U.S.C. 154(b) by 0 days.

(21) Appl. No.: 09/606,056

(22) Filed: Jun. 28, 2000

Related U.S. Application Data

(63) Continuation of application No. 09/198,000, filed on Nov. 23, 1998, now abandoned.

(30) Foreign Application Priority Data

Nov. 24, 1997 (FR) .................................................. 97 14728

(51) Int. Cl.[7] ...................................................... C12M 1/00

(52) U.S. Cl. ..................................... 435/307.1; 435/287.7; 435/288.1

(58) Field of Search .............................. 435/283.1, 287.1, 435/287.7, 288.1; 422/100, 102

(56) References Cited

U.S. PATENT DOCUMENTS 4,558,014 * 12/1985 Hirschfeld .
5,190,880 3/1993 Cassou et al. ........................ 435/296
5,283,170 2/1994 Cassou et al. ............................ 435/1

FOREIGN PATENT DOCUMENTS 995878 8/1951 (FR) .
1488345 6/1967 (FR) .
2539628 7/1984 (FR) .
2651793 3/1991 (FR) .
2762210 10/1998 (FR) .

* cited by examiner

*Primary Examiner*—David A. Redding
(74) *Attorney, Agent, or Firm*—Morgan & Finnegan LLP

(57) ABSTRACT

A straw for the conservation of small quantities of substances, notably biological substances, comprising a segment of tube fitted internally at one end with an insert through which there is a substantially coaxial orifice. A plug can be accommodated in the insert.

8 Claims, 1 Drawing Sheet

STRAW WITH ADAPTER INSERT

This is a continuation of application Ser. No. 09/198,000 filed Nov. 23, 1998 now abandoned.

BACKGROUND OF THE INVENTION

1. Field of the Invention

The present invention relates to a straw for the conservation of small quantities of substances, notably biological substances, in particular biological liquids.

2. Description of the Prior Art

This type of straw, known under the term "French straw", was disclosed for the first time in French patent No. 995 878.

The straws used up to now included a tripartite plug consisting of two pads of a fibrous substance enclosing a powder capable of being transformed in contact with a liquid into an impermeable gel or paste adhering to the wall of the tube, creating a tight stopper.

The tripartite plug straws we have developed and marketed give entire satisfaction. Nevertheless, a certain absorption of liquid contained in the straw may have been found, although very low.

There are straws with different diameters. For straws with a large diameter, for example 3.7 mm, the tripartite plug will be larger and there will be much more absorption. It is therefore desirable not to use a larger plug for a larger diameter straw.

For obvious reasons of economic production, it would generally be advantageous to be able to use plugs of similar sizes for straws with different diameters, regardless of the nature of the plug.

One aim of the invention is to provide a straw including a device enabling the same size plug to be used regardless of the diameter of the straw.

Other aims and advantages of the invention will become apparent upon reading the following description.

SUMMARY OF THE INVENTION

The present invention achieves the above aim and provides a straw for the conservation of small quantities of substances, notably biological substances, comprising a segment of tube fitted internally at one end with an insert through which there is a substantially coaxial orifice.

The insert is usually made of a material selected from elastomer materials, thermoplastics materials and thermoplastics elastomer material. It can equally be made of metal or any other appropriate material.

The plug of the straw is accommodated in the insert if necessary.

The plug can be a tripartite plug, a one-piece plug or constituted in some other way.

A capillary insert can equally be provided so that the straw can be used without any plug. The insert can then serve also as a filling indicator.

The end of the straw that does not incorporate the insert in accordance with the invention normally remains open for filling it with the product to be conserved, which is usually a liquid.

To protect the product from contamination the open end is closed, for example welded closed, in particular using ultrasound or thermal welding, or by any other appropriate technique known to the skilled person.

It is advantageous to be able to "color code" the straws without using straws that are themselves colored. In accordance with the invention this can be achieved by choosing an insert made from a colored thermoplastics material or a colored thermoplastics elastomer material.

In the embodiment in which the insert is adapted to receive a plug, the diameter of the inside orifice of the insert is usually, but not exclusively, in the range approximately 1.6 mm to approximately 2.5 mm.

In the embodiment in which the insert is not intended to receive a plug, that is to say when the insert is a capillary insert, it usually, but not exclusively, has a diameter in the range approximately 0.5 mm to approximately 2 mm.

The invention will now be described by way of non-limiting example and with reference to the accompanying drawings.

DETAILED DESCRIPTION OF THE PREFERRED EMBODIMENTS

Figure 1:
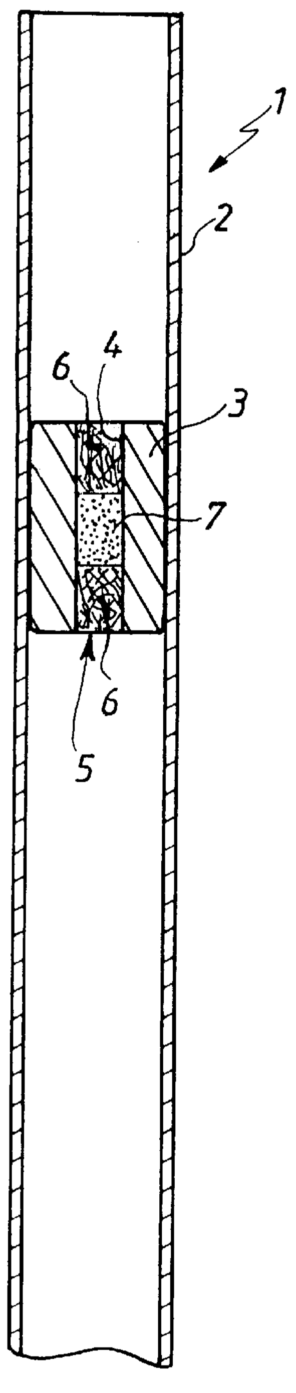
FIG. 1 is a view in longitudinal section of one embodiment of a straw in accordance with the invention.

In FIG. 1, the straw 1 comprises a segment of tube 2 fitted with the insert 3 through which passes a substantially coaxial orifice 4 in which is accommodated a tripartite plug 5. The tripartite plug 5 comprises powder 7 between two layers of cotton 6.

Figure 2:
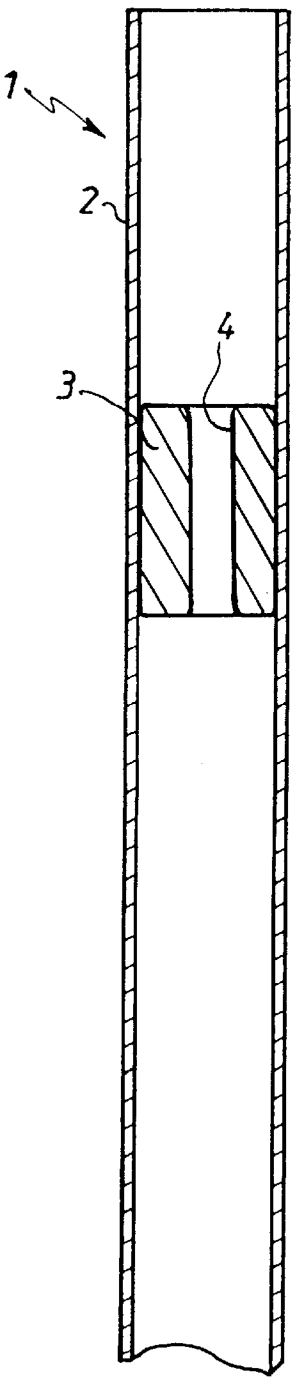
FIG. 2 is a view in longitudinal section of another embodiment of a straw in accordance with the invention.

In FIG. 2, the straw 1 comprises a segment of tube 2 fitted with the insert 3 through which there is a substantially coaxial capillary orifice, but not fitted with a plug.

The skilled person will understand that although the invention has been described and illustrated with reference to particular embodiments, many variants are feasible that remain within the scope of the invention as defined in the accompanying claims. In particular, the plug that may be accommodated in the insert need not be a tripartite plug. For example, the plug can be made of microporous solid fiber, as described in copending patent application FR-A-97 04896.

What is claimed is:

1. A straw for the conservation of small quantities of biological substances, comprising a segment of tube fitted internally at one end with an insert through which there is a substantially coaxial orifice.

2. The straw claimed in claim 1 wherein said insert is made of a material selected from elastomer materials, thermoplastics materials and thermoplastics elastomer materials.

3. The straw claimed in claim 1 wherein said insert is made of metal.

4. The straw claimed in claim 2 wherein said insert is colored.

5. A straw as claimed in claim 1 wherein a plug is accommodated in said insert.

6. The straw claimed in claim 5 wherein said plug is a tripartite plug.

7. The straw claimed in claim 5 wherein said plug is a one-piece plug.

8. The straw claimed in claim 1 wherein said insert is a capillary tube.

* * * * *